United States Patent [19]

Okubo et al.

[11] Patent Number: 5,565,978
[45] Date of Patent: Oct. 15, 1996

[54] TOTAL-REFLECTION TYPE REFRACTIVE INDEX SENSOR

[75] Inventors: Shuichi Okubo, Tokyo; Yasushi Nagasawa; Kazunari Naya, both of Saitama, all of Japan

[73] Assignee: Japan Energy Corporation, Tokyo, Japan

[21] Appl. No.: 356,233

[22] PCT Filed: Mar. 24, 1994

[86] PCT No.: PCT/JP94/00470

§ 371 Date: Dec. 13, 1994

§ 102(e) Date: Dec. 13, 1994

[87] PCT Pub. No.: WO94/24543

PCT Pub. Date: Oct. 27, 1994

[30] Foreign Application Priority Data

| Apr. 15, 1993 | [JP] | Japan | 5-111169 |
| Dec. 14, 1993 | [JP] | Japan | 5-342016 |
| Feb. 8, 1994 | [JP] | Japan | 6-34220 |

[51] Int. Cl.⁶ .................................................. G01N 21/41
[52] U.S. Cl. ........................... 356/128; 356/133; 356/136
[58] Field of Search ................................. 356/128–137; 385/12, 14, 129

[56] References Cited

U.S. PATENT DOCUMENTS

| 4,950,074 | 8/1990 | Fabricius et al. | 356/133 |
| 5,165,005 | 11/1992 | Klainer et al. | 356/128 |

FOREIGN PATENT DOCUMENTS

| 3929340 | 3/1991 | Germany | 385/14 |
| 4038791 | 8/1991 | Germany | 356/128 |
| 58-27044 | 2/1983 | Japan . | |
| 60-66137 | 4/1985 | Japan | 356/133 |
| 60-76646 | 5/1985 | Japan | 356/133 |
| 60-90062 | 6/1985 | Japan . | |
| 61-11637 | 1/1986 | Japan . | |
| 62-49240 | 3/1987 | Japan . | |
| 63-500263 | 1/1988 | Japan . | |
| 63-144239 | 6/1988 | Japan . | |
| 63-132139 | 6/1988 | Japan . | |
| 63-201547 | 8/1988 | Japan . | |
| 1-197633 | 8/1989 | Japan . | |
| 1-270646 | 10/1989 | Japan . | |
| 1-282448 | 11/1989 | Japan . | |
| 2-114151 | 4/1990 | Japan . | |
| 2-236146 | 9/1990 | Japan . | |
| 2-60259 | 12/1990 | Japan . | |

OTHER PUBLICATIONS

ATAGO Catalog for Process Refractometer (11 Pages). undated.

*Primary Examiner*—F. L. Evans
*Attorney, Agent, or Firm*—Panitch, Schwarze, Jacobs & Nadel, P.C.

[57] ABSTRACT

A refractive index sensor of a total-reflection type comprises a waveguiding layer of a cladding/core/cladding waveguide structure formed on a substrate. The waveguiding layer has an input face connected to either a single optical fiber or a plurality of optical fibers for injecting a light(s) into the layer, a detection face which, obeying Snell's law, totally reflects/transmits the light beam or beams that have arrived there with an expansion angle from the optical fiber or fibers and which constitutes a surface with which a material whose refractive index is to be measured comes in contact, and an output face which outputs the light reflected from the detection face and is connected to an optical detector. The refractive index of the material of interest is detected from a bright-dark boundary of the presence of the corresponding total reflected light from the detection face. With no need of a bulk prism or lamp-type light source, the sensor is small in size and high in sensitivity.

20 Claims, 12 Drawing Sheets

FIG. 7
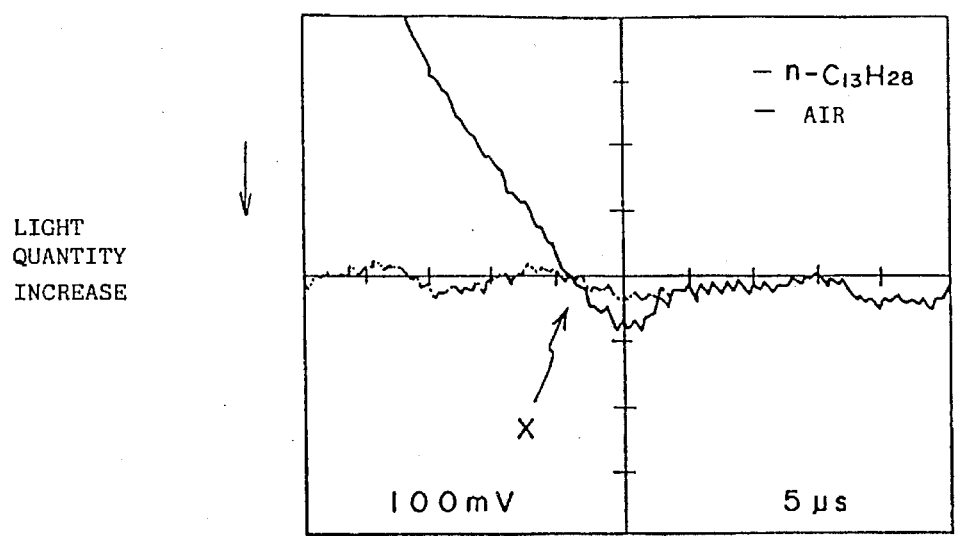
LIGHT QUANTITY INCREASE
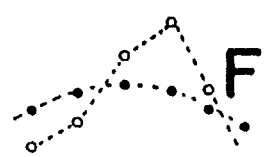
FIG. 8(a)
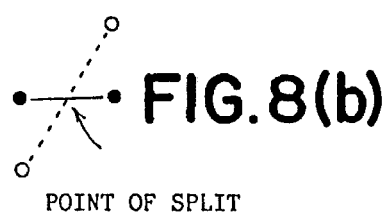
FIG.8(b)
POINT OF SPLIT
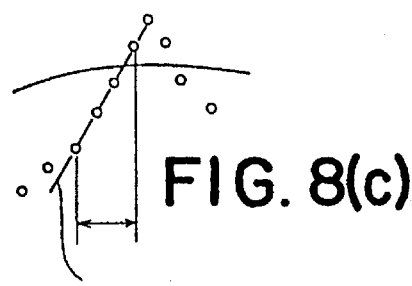
FIG. 8(c)
REGRESSION CURVE
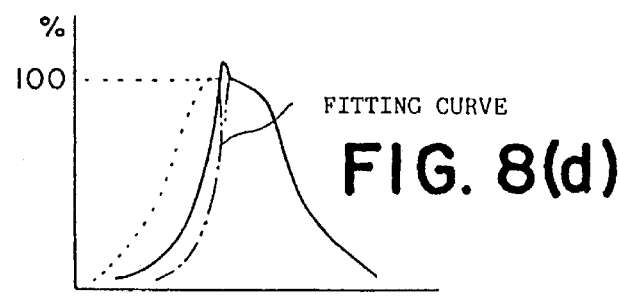
FIG. 8(d)

TOTAL-REFLECTION TYPE REFRACTIVE INDEX SENSOR

TECHNICAL FIELD

This invention relates to a refractive index sensor of a total-reflection type, and more specifically to a compact, high-precision refractive index sensor of a total-reflection type which uses a single optical fiber or a plurality of optical fibers and includes a waveguiding layer of a cladding/core/cladding waveguide structure formed on a substrate.

BACKGROUND ART

Determination of refractive indices is frequently needed in industrial operations, typically in identifying a substance, measuring the concentration of a solution or liquid mixture, measuring a contaminant concentration in a certain material, and in monitoring the formation of a deposit or precipitate in a solution, the progress of reaction in a liquid, or the extent of polymerization reaction. For example, refractive index determination on site is in practice in the petroleum industry to determine the concentration of a petroleum component possibly mixed in an objective petroleum product, such as the concentration of butane that is likely to mix into octane during the production of the latter. The refractive index of octane is 1.39 and that of butane is slightly lower at 1.34. Mixing of butane into octane lowers the refractive index below the level of genuine octane, accordingly as the butane percentage increases. The refractive index reading thus tells how much butane has been mixed in. Process refractometers are in use elsewhere, e.g., in controlling the mixing of syrups with water for drinks and in controlling the polymerization processes for the preparation of polymers. Refractometers are also used in other fields, e.g., in the manufacture of pharmaceuticals, spices and flavors, oils and fats, fermentation products, and surfactants.

There are some known refractometers designed for the measurement of refractive indices. Abbe refractometer sandwiches a liquid whose refractive index is to be measured between the opposing inclined planes of two right-angled prisms, thus forming a liquid layer of about 0.1 mm thickness, and measures the angle of outgoing light through it corresponding to the critical angle. Being a transmission type, Abbe refractometer cannot be used for dark colored samples. It also requires the injection of a sample into between the opposing inclined planes of two right-angled prisms. For these reasons the refractometer is not practically useful for continuous monitoring at the site of commercial production.

An alternative approach is the refractometer of a total-reflection type. For example, a refractive densitometer for lubricating oils is marketed by Electromachine Co., the U.S., under the trade designation of "Model SSR-72." Light from a source is led through a condenser lens to form parallel light beams, while a motor-driven scanner with a spiraled slit revolves to scan the condenser lens, so that the light is injected into a bulk prism having a surface in contact with a fluid being measured, and the reflected light is determined by a detection unit. The instrument makes use of the phenomenon that light incident at angles smaller than the critical angle refract in a sample solution but the light rays at angles larger than the critical angle are totally reflected by a prism plane toward detection means.

A refractometer utilizing a bulk prism is on sale by ATAGO Co. as a process refractometer of PRM series. A block diagram of its detection unit is shown in FIG. 12 as a reprint from the manufacturer's Catalog Nos. 3621 and 3670. The detection unit is located on a part of a process line to detect the refractive index of the liquid flowing through the line. Light from a light source 30, such as a tungsten lamp or halogen lamp, is injected into a bulk prism 32. The bulk prism is trapezoidal, and the light is reflected on one side and is transmitted through or is totally reflected by a detection face 33 in contact with a sample liquid. In case of total reflection, the reflected beam is led through a lens and a light receiver 34 and is sent to an electric circuit 36. The electric circuit is connected with thermistors 40, 42, a humidity sensor 44, and a power supply circuit 46 so that it can yield refractive index, temperature, and various alarm outputs.

The above-mentioned refractive densitometer Model SSR-72 requires a lamp-type light source, motor-driven beam scanning mechanism, condenser lens, bulk prism, detector, etc. It therefore cannot be made small in size and is inconvenient for actual use. Another disadvantage is a large heat capacity. Further, because it includes moving parts, care must be taken in its operation and maintenance. ATAGO's process refractometer again includes a lamp-type light source and a bulk prism, which make size reduction impossible. When the bulk prism is used, the heat capacity is so large that much time is required before thermal stabilization is achieved, and hence a long measurement time is required. At a bulk prism, the light expands to such an extent that detection involves difficulties. The employment of a lamp as a light source causes a parallax, bringing the detection end (boundary) out of focus and reducing the measurement accuracy.

The present invention has for its object to develop a small, high-precision refractive index sensor of a total-reflection type which requires neither bulk prism nor lamp-type light source.

DISCLOSURE OF INVENTION

We perceived the fact that the phenomenon inherent to a single-mode optical fiber wherein the light leaving the fiber expands to an angle of about 6 to 8 degrees. We then conceived of combining that optical fiber with a waveguiding layer composed of a cladding/core/cladding waveguide structure formed on a substrate to fabricate a refractive index sensor of a total-reflection type. A prototype proved to perform satisfactorily. It has also been confirmed that incorporation of a plurality of such optical fibers having individual incident angles broadens the refractive index measurement range without any sacrifice of the measurement accuracy.

On the basis of these findings, the present invention provides a refractive index sensor of a total-reflection type characterized by a waveguiding layer of a cladding/core/cladding waveguide structure formed on a substrate, said waveguiding layer having an input face connected to either a single optical fiber or a plurality of optical fibers which differ in angle of incidence but altogether form a continuous incident angle range for injecting a light into said waveguiding layer, a detection face which totally reflects/transmits the incident light having an expansion angle from the optical fiber or fibers and which constitutes a surface with which a material whose refractive index is to be measured comes in contact, and an output face which outputs the light reflected from the detection face and is connected to optical detection means, whereby the refractive index of the material is detected from the presence of the corresponding total reflected light from the detection face.

The refractive index sensor of the total-reflection type according to this invention may also embodied as (1) a structure of single-reflection type wherein the light from the input face is directly incident on the detection face, where the light is totally reflected/transmitted, and the reflected light from the detection face directly reaches the output face or (2) a structure of plural-reflection type wherein the light from the input face is totally reflected once or more times before incidence on the detection face, where it is totally reflected/transmitted, and the reflected light from the detection face arrives at the output face either directly or after total reflection once or more times. As an example of the plural-reflection type may be included (3) a structure of triple-reflection type wherein the input face and output face are combined flush with each other to be an input/output face parallel to the detection face, and the light from the incidence position of the input/output face is totally reflected on one side to the detection face, where it is totally reflected/transmitted, and the reflected light from the detection face is totally reflected on another side to reach the output position of the input/output face.

Moreover, (A) the expansion angle of the light from the optical fiber can be adjusted by working the end shape of the fiber, (B) a waveguiding layer lens can be provided adjacent to the input face, inside the waveguiding layer, or close to the output face, and (C) the detection face can be worked to a concave or convex contour so as to adjust the refractive index range. As for the optical detector, the use of a CCD photosensor or CCD photosensor array is desirable. It is recommended that the optical detection means includes a measurement/computation unit which determines a bright-dark boundary using the linear interpolation, polynomial-curve interpolation, or fitting method.

BRIEF DESCRIPTION OF THE DRAWINGS

FIG. 7 is a graph showing the detail of a bright-dark boundary position portion when the quantity of reflected light on an air surface is measured as a reference wave form and the quantity of reflected light from $n-C_{13}H_{28}$ placed as a sample in a cell is measured;

FIG. 8 illustrates how the point of intersection of a reference and measured light beams is found, (a) by giving exemplary output values in pixels around the intersection point, (b) by linear interpolation, (c) by multi-curve interpolation, or (d) by fitting;

BEST MODE FOR CARRYING OUT THE INVENTION

A refractive index sensor of total-reflection type operates on a principle that whereas the lights incident on a boundary surface between two media of different refractive indices, from a medium 1 (with a refractive index $n_1$) to a medium 2 (a refractive index $n_2$), are refracted in conformity with Snell's law, the lights incident at angles greater than a critical angle $\theta_c$ (degree) defined as $\sin \theta_c = n_2/n_1$ are totally reflected. The emitted light from a single-mode optical fiber connected to the input face has a characteristic expansion ($\pm \Delta$) (degree). While maintaining that expansion, the light travels through a waveguiding layer to reach a detection face in contact with an object to be examined, with a certain expansion ($\alpha \pm \Delta$) (degree) centered on a central incident angle of $\alpha$ degree. If the critical angle $\theta_c$ of the object is in the range ($\alpha \pm \Delta$), the refractive index can be determined by measuring the intensity of light at the output face by a photodetector such as a CCD photosensor and thereby ascertaining the bright-dark boundary position, because the reflection conditions vary with the two sides of the critical angle $\theta_c$ of the object as the borderline. The term "bright-dark boundary" as used herein means the boundary between a region of total light reflection and a region where light is not totally reflected but is partly transmitted and reflected. Only if the central incident angle α is chosen properly to agree with the critical angle $θ_c$ of the object or thereabouts, it becomes possible to measure the desired refractive index range centered around the critical refractive index corresponding to the critical angle $θ_c$.

The combination of a waveguiding layer of a waveguide structure of cladding/core/cladding on a substrate with optical fibers and a laser light source renders it possible to provide a refractive index sensor very small in size and high in precision. As the sensor is thermally stabilized in a short time, it requires only a short measuring period. By setting the thickness of the waveguiding layer to the conditions of single mode, the light intensity can be trapped in the core, making it easy to detect the reflected light. Core layers with varied refractive indices can be formed with ease, and requirements for measuring the objects of different refractive indices can be met. The use of a laser beam as a light source permits limitation of the blur at the detection end. In addition, it enhances the accuracy of measurement through precise discrimination of the bright-dark boundary. It is further possible to attach a plurality of optical fibers to the incidence side of the waveguiding layer, allot separate measurement ranges to the individual optical fibers, and overlap the measured values, whereby the measurement range can be broadened without a decrease of measurement precision.

Figure 1:
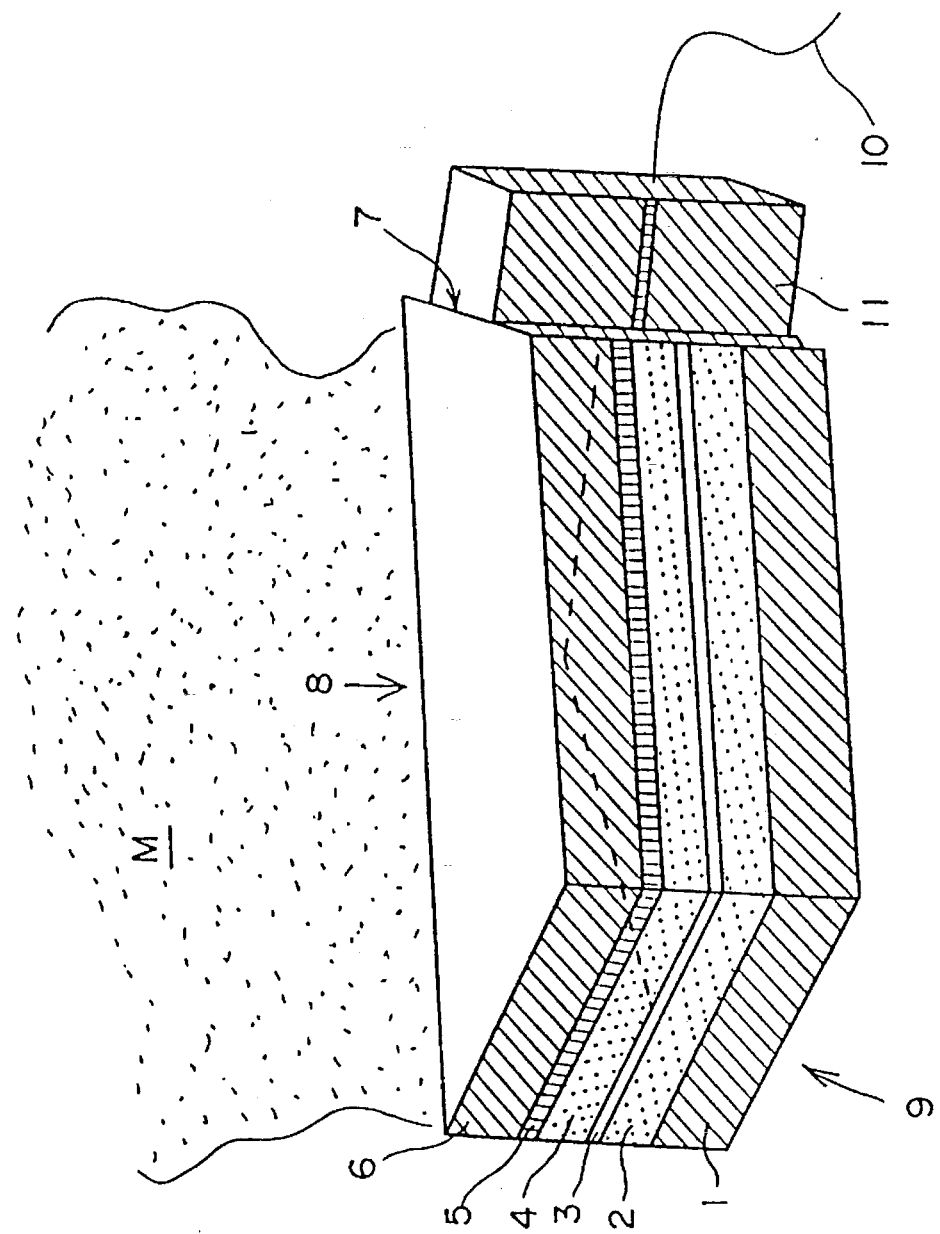
FIG. 1 is a perspective view, in section, of essential parts of a total-reflection type photosensor of a single reflection structure which uses a single optical fiber, as an embodiment of the present invention.

FIG. 1 is a perspective view of essential parts of an embodiment of the total-reflection type photosensor according to this invention. The total-reflection type photosensor is a laminated structure fabricated by forming films of cladding glass 2, core glass 3, and cladding glass 4 on a substrate 1 so as to form a waveguiding layer of a cladding/core/cladding waveguide structure on the substrate, and then affixing another substrate 6 to the waveguiding layer through a layer of adhesive 5. The lower substrate 1 and the upper substrate 6 are typically made of silicon. On the lower substrate 1 are formed the glass portions 2, 3, and 4 of commonly used glass materials by a conventional film-forming technique such as chemical vapor deposition or sputtering. The cladding glass films 2 and 4 are formed, e.g., from $SiO_2$ and the core glass 3, e.g., from $SiO_2$ and $GeO_2$. The adhesive that may be used is, e.g., an epoxy resin. This laminated structure has an input face 7 for injecting a light into the waveguiding layer which is made up of the cladding/core/cladding glass portions 2, 3, and 4, a detection face (at the rear of the drawing) 8 which reflects/transmits the incident light and constitutes a surface for contact with a material whose refractive index is to be determined, and an output face 9 from which the reflected light emerges or outgoes. The detection face 8 is designed to be in contact with the object. The input face 7 is connected to an optical fiber array 11 through which an optical fiber 10 is inserted. The optical fiber, in turn, is connected to a light source such as a GaAs—AlGaAs or other semiconductor laser or He—Ne laser. To the output face 9 is connected an optical detection means using, e.g., a CCD photosensor (not shown in FIG. 1). The optical detection means is desirably equipped with a measurement/computation unit (not shown in FIG. 1) for clearer distinction of the bright-dark boundary of detected light. This embodiment is called a single-reflection type refractive index sensor because the light incident from the optical fiber is once reflected by the detection face to reach the output face.

Figure 2A:
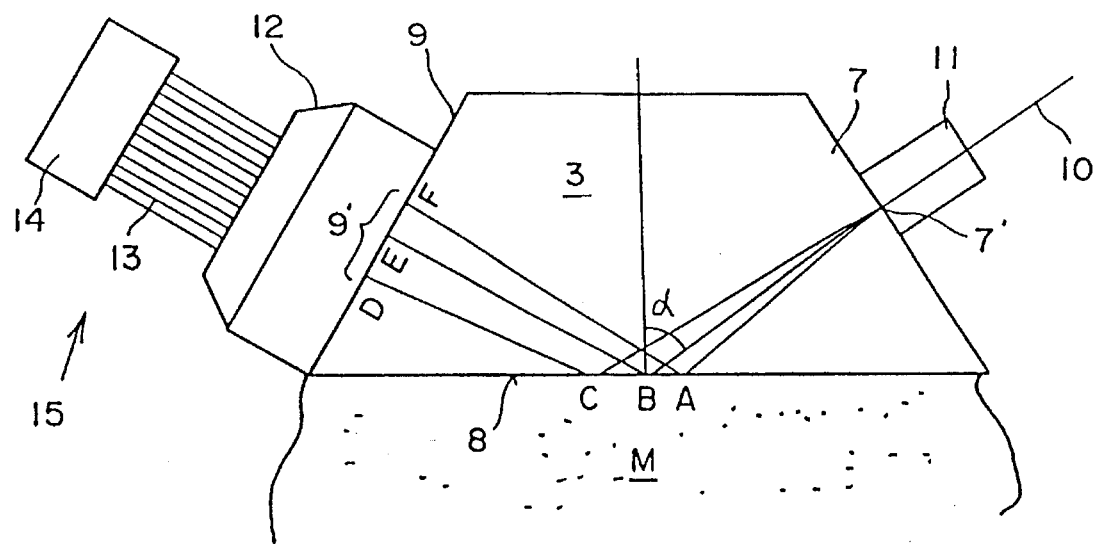
FIG. 2 explains the operating principle of the total-reflection type photosensor of a single reflection structure using a single optical fiber shown in FIG. 1 as an embodiment of the invention, (a) showing a core glass waveguiding layer of FIG. 1, and (b) being a graph which shows the relation between the output position of a CCD photosensor and the refractive index.

FIGS. 2(a) and (b) schematically illustrate the operating principle of the embodiment of FIG. 1, a photosensor of a total-reflection type according to this invention. FIG. 2(a) shows the core glass waveguiding layer of FIG. 1. A light from the single-mode optical fiber 10 reaches a light incidence position 7' of the input face 7 through the optical fiber array 11. The emitted light from the optical fiber expands naturally over an angle of about 6 to 8 degrees, and thence, while maintaining the expansion of about 6 to 8 degrees ±Δ, travels through the waveguiding layer to arrive at the detection face 8 in contact with an object M whose refractive index is to be determined, with a certain expansion (α±Δ) centered around the central incident angle α. The center of the arrival spot is indicated at B and the both extremities at A and C. If the lights are totally reflected from the detection face, the lights from the points A, B, and C reach the points D, E, and F, respectively, of a light outgoing position 9' of the output face 9. A photodetector 12 such as a CCD photosensor array detects the outgoing lights among the points D, E, and F. For accurate distinction of the bright-dark boundary of the emerging light, signal lines 13 are connected to a measurement/control unit 14. These components, i.e., photodetector 12, signal lines 13, and measurement/computation unit 14, constitute an optical detection means 15.

Figure 2B:
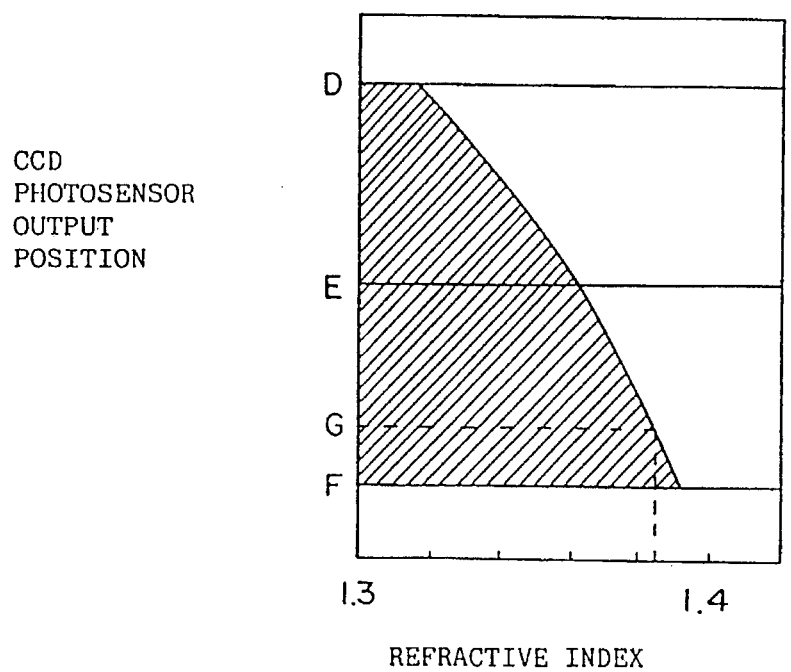

For example, this sensor is used in monitoring the limiting butane concentration in a liquid mixture of butane (refractive index: 1.34) and octane (refractive index: 1.39) to see the concentration of butane that can mixed as an impurity into octane during the production of the latter. In that case, the angle of incidence of the point A is set to 65° (critical refractive index: 1.320), that of the point B to 69° (critical refractive index: 1.365), and that of the point C to 73° (critical refractive index: 1.395), so as to secure a refractive index measurement range of 1.320 to 1.395. The cladding layers are about 20 μm thick, the core layer is about 8 μm thick, and the length of optical path for the emitted light from the optical fiber is 39 mm. An He—Ne laser with a wavelength of 632.8 nm is used as a light source. The light expansion angle is 8° and the refractive index of the waveguiding layer is 1.458. FIG. 2(b) graphically represents the CCD photosensor output position versus the conditions for total reflection. Here the refractive indices in the range from 1.320 to 1.395 centered around the index 1.365 can be detected. Thus, the graph shows that, as the proportion of mixing butane into octane increases and the refractive index of the liquid mixture decreases, the resulting reflection conditions gradually shift toward the D side of the light-output spot of the CCD photosensor. For example, at the point of time when it is detected at the point G that the refractive index has just reached 1.385, a proper step is taken to control the octane manufacturing process in order to prevent a further increase in the butane content.

Figure 3:
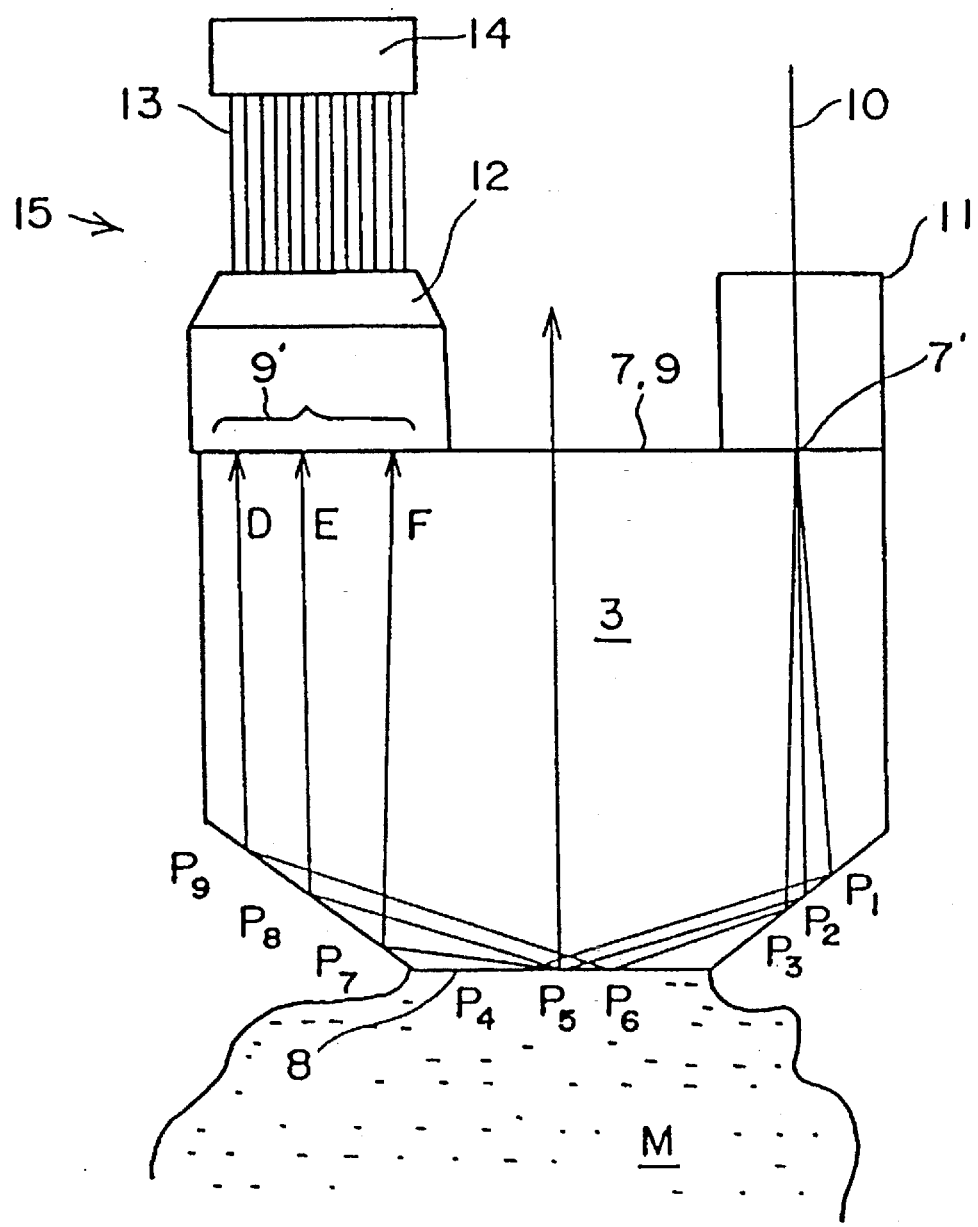
FIG. 3 is a top view of a modified form of core glass waveguiding layer of an embodiment of the total-reflection type photosensor of a triple-reflection type according to this invention.

FIG. 3 shows an embodiment of the core glass waveguiding layer of a refractive index sensor of a triple-reflection type according to this invention as an example of a type involving a plurality of times of reflection, unlike the embodiment of a single-reflection type refractive index sensor shown in FIGS. 1 and 2. Like reference numerals are used to denote parts like those shown in FIG. 2. Here, the input face and the output face may be combined to be a common input/output face 7,9 parallel to the detection face. A light from a single-mode optical fiber 10 travels through an optical fiber array 11 to reach a light incidence point 7' of the input/output face 7,9. The beam from the optical fiber naturally expands over an angle of about 6 to 8 degrees thence, while maintaining the expansion of about 6 to 8 degrees, travels substantially vertically down the waveguiding layer to arrive at points $P_1$, $P_2$, and $P_3$ on the opposite side. The lights are totally reflected there to reach points $P_4$, $P_5$, and $P_6$, respectively, of a detection face 8 in contact with an object M whose refractive index is to be determined, with a certain expansion ($\alpha \pm \Delta$) centered around an angle of incidence $\alpha$. If it is assumed that the lights are totally reflected from the detection face, they reach points $P_7$, $P_8$, and $P_9$ of another adjoining side, from whence they are totally reflected back to points D, E, and F, respectively, of a light-output spot 9' of the input/output face 7,9. As is the case with the preceding embodiment, a photodetector 12 such as a CCD photosensor array detects the emerged lights among the points D, E, and F. Signal lines 13 are connected to a measurement/computation unit 14. The photodetector 12, signal lines 13, and measurement/computation unit 14 constitute an optical detection means 15.

An example of fabrication thereof will now be explained. Claddings and core of a waveguiding layer are made in the form of cladding layers of $SiO_2$ (refractive index: 1.458) 20 μm thick each and a core layer of $SiO_2.GeO_2$ (refractive index: 1.465) 6 μm thick. They were formed as films by CVD on a 1 mm-thick silicon substrate. A thermosetting plastic adhesive was applied to the top face and a 1 mm-thick silicon substrate was bonded to the laminate and then the adhesive was set by heating at about 125° C. The laminated structure was diced by a dicing machine, and the input/output face and the detection face were optically polished. The vertical distance between the input/output face and the detection face was 15 mm. The incident-light expansion angle being 6° and the central light incident angle 67.5, the width of the output spot D-E-F when out of contact with a test material was about 6 mm. The measurable refractive index range was 1.32 to 1.38.

The triple-reflection type offers the following advantages:

(1) Since the light is returned back by the detection face, the optical path length can be approximately twice that of the single-reflection type, with a sensor head of about the same size. This broadens the width of emerging light at the CCD photosensor array, thus enhancing its resolving power for measurement.

(2) The sensor is constructed so that a light beam travels perpendicularly through the input face and outgoes perpendicularly through the output face. The input face and output face can be flush with each other on a common plane, and both the incident-light optical fiber and optical fiber array can be mounted on the same side as the CCD photosensor array, opposite to the detection face. The arrangement makes the whole construction compact and suitable for continuous process measurement. The fact that the input-output region and the detection region can be spaced apart is an expedient to system designing.

(3) When the temperature of the detection face is to be controlled, the triple-reflection type that has the incidence optical fiber, optical fiber array, and CCD photosensor array, all located on the opposite side of the detection face, is easier to perform the control than the single-reflection type.

Figure 4:
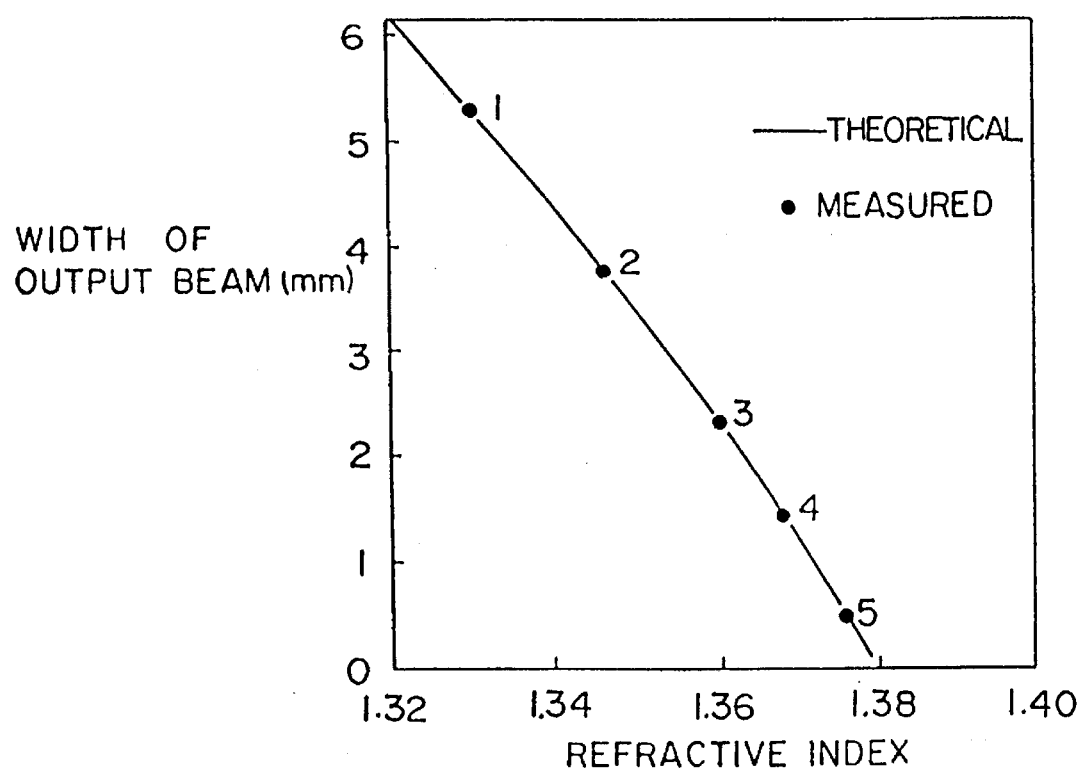
FIG. 4 is a graph giving theoretical values and actually measured values in the measurement of refractive indices of (1) methanol, (2) methanol+ethanol, (3) ethanol, (4) ethanol+isopropanol, and (5) isopropanol by an experimentally manufactured sensor of a triple-reflection type.

The results of measurements made using this triple-reflection type sensor are graphically shown in FIG. 4. The light source was a GaAs—AlGaAS laser (wavelength: 0.85 μm). The test materials, five in all, were methanol, methanol-ethanol mixture, ethanol, ethanol-isopropanol mixture, and isopropanol. The theoretical values were found from optical path computation, and the actual measurement values are the emerging light widths obtained by this sensor and assigned to the refractive indices of the individual liquids given in the literature. As can be seen from the graph, the theoretical values (in a solid curve) and actual values (in dots) are in good agreement. The service temperature range of the sensor was broad enough, from room temperature to 80° C., to perform measurements with fast response. The sensor temperature was measured with a thermocouple secured to one side of the sensor body.

In the triple-reflection type sensor, the light beam from the input face is totally reflected once each before and after the incidence on the detection face. A variation of this type may be used instead which involves a plurality of reflections so that the light beam is totally reflected twice before incidence on the detection face and then is directly led to the output face.

Figure 13:
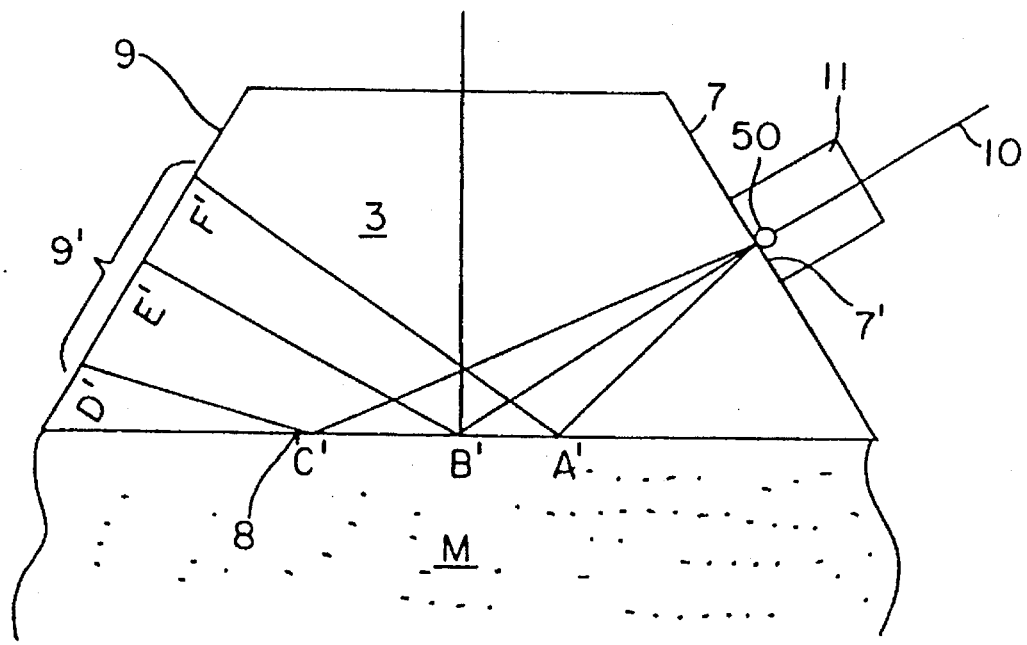
FIG. 13 shows a waveguiding layer lens provided between the optical fiber and input face of the waveguiding layer of FIG. 2.
Figure 14:
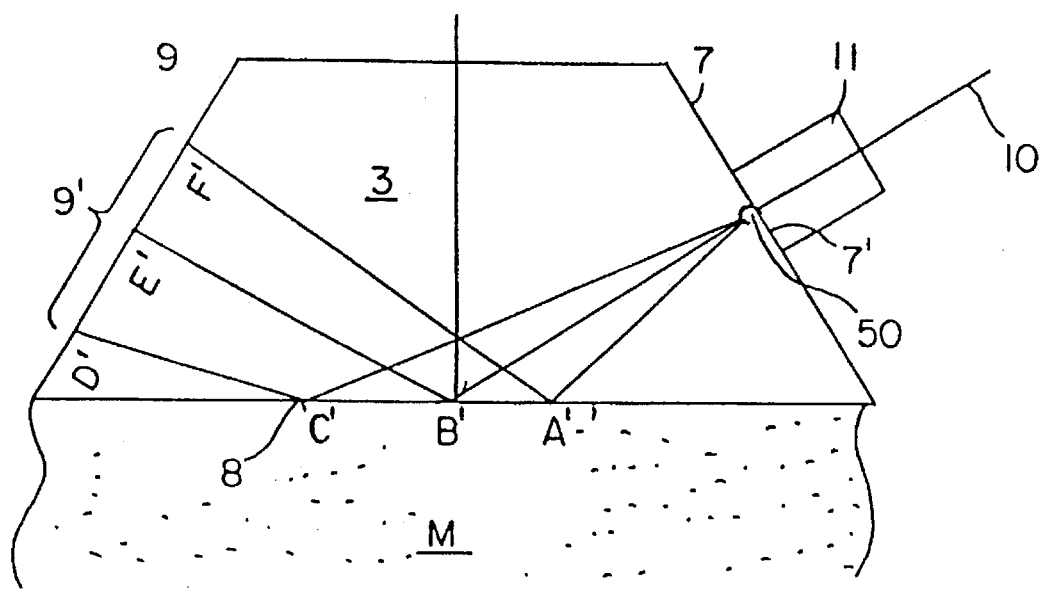
FIG. 14 shows a waveguiding layer lens provided inside of the waveguiding layer of FIG. 2.

This invention makes use of the angle of expansion of the light emitted from a single-mode optical fiber. The expansion angle can be altered by working the end of the optical fiber, e.g., by melt processing or etching to a hemispherical lens or rounded-tip tapered shape. Also, adjustments over a broad range are made possible by locating waveguiding layer lenses such as optical fiber type lens/self-focusing (SELFOC) lens (50) adjacent to the input face (FIG. 13), inside the waveguiding layer (FIG. 14), or close to the output face. The refractive index range can be broadened by working the detection face to a concave contour or can be narrowed by making it convex.

Possible means of broadening the measurement range, as noted above, include:

(1) Working the end configuration of the optical fiber so as to increase the expansion angle of the fiber;

(2) Interposing a waveguiding layer lens (50) between the optical fiber and the input face to enlarge the fiber's expansion angle (FIG. 13); and (3) Concavely shaping the detection face.

When the expansion angle ($\pm \Delta$) of emitted light from the optical fiber is increased, as in (1) or (2), the width of the emitted light beam increases too. This necessitates extension of the length of the detection face and that of the optical detection means as well, no longer allowing the sensor to be small in size. With the means (3), the width of the light on the detection face is about equal to the conventional width, and there is no need of increasing the length of the detection face. However, the emitted light having a broad incident angle is reflected with the same width as the emitted light of the ordinary incident angle, and therefore the sensor has low accuracy compared with conventional sensors.

Figure 5A:
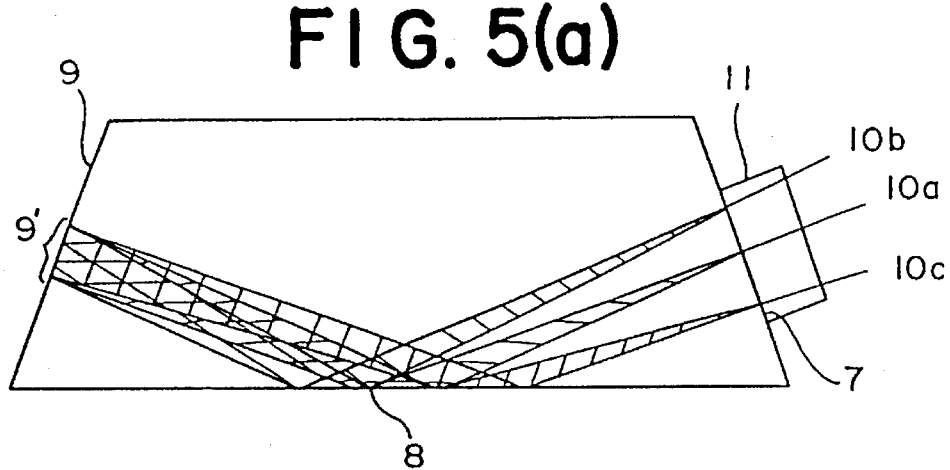
FIG. 5 schematically illustrates a sensor of a single-reflection type using a plurality of optical fibers, (a) when the points of intersection of optical axes of beams emergent from those optical fibers are arranged to be at one spot of the output face of the waveguiding layer, (b) when those intersection points are arranged to be at one spot of the detection face of the waveguiding layer, or (c) when the angle of expansion of an optical fiber is increased to such an extent that a single optical fiber obtains the same incident angle range as in the case (a) or (b) above.
Figure 5B:
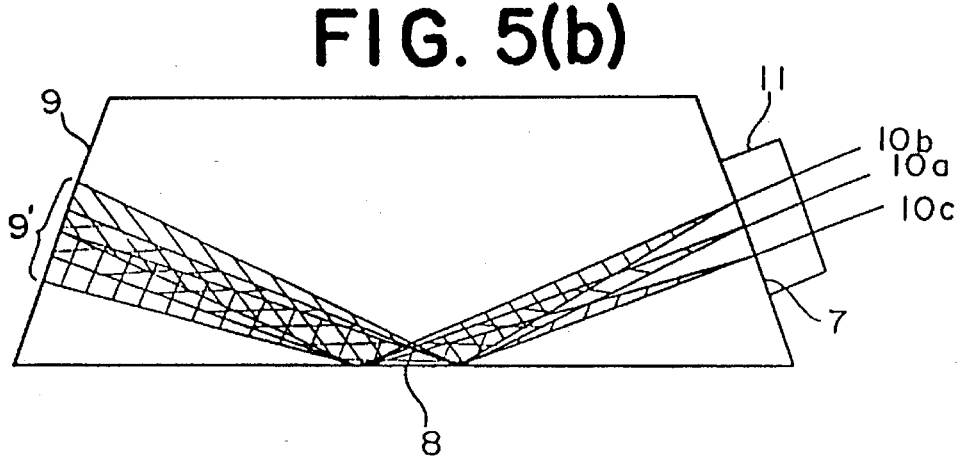

Thus, in still other embodiments of this invention, as illustrated in FIGS. 5 and 6, a plurality of optical fibers ranging in number from two to five, e.g., three optical fibers 10a, 10b, and 10c can be attached to an input face 7 through an optical fiber array 11 so as to have different incident angles to a detection face. The measurement range can be broadened without a reduction of the measurement accuracy, by attaching the plurality of optical fibers to the incidence side of a waveguiding layer, assigning separate ranges of measurement to the individual optical fibers, and overlapping those ranges. For example, if three optical fibers with an expansion angle of the measurable range of emitted light of 4° each are set to have incident angles of 65°, 69° and 73° to the detection face, it becomes possible to set an overall incident angle range of 63° to 75° and measure refractive indices within the range corresponding to that overall range. When a measurement is to be made in this way, it is only necessary to choose optical fibers corresponding to the total reflection angle ($\theta_c$) of the test material.

In FIG. 5, there is shown schematically a total-reflection type refractive index sensor of a single-reflection type structure as in FIG. 2, with the optical axes of emitted light from three optical fibers having an expansion angle width of 4° each intersecting at one spot of the detection face 8(a) or intersecting at one spot of the output face 9(b). For reference, an alternate arrangement using a single optical fiber with an expansion angle of 12°, equal to the combined expansion angles of three optical fibers, is schematically shown at (c). Thus, a plurality of optical fibers permit narrowing the width of the emitted light beam compared with a single optical fiber of a large expansion angle. Especially when the optical axes of the light beams intersect at one spot of the output face, the width of the outgoing light can be narrowed down.

An example of fabrication of a single-reflection type refractive index sensor using three incidence optical fibers whose optical axes intersect at one spot of the output face as indicated in FIG. 5(a) will now be explained. The ends of the optical fibers were worked by polishing so that the emitted light from the fibers have an expansion angle of 6° each. A waveguiding layer consisted of 20 μm-thick cladding layers of $SiO_2$ (refractive index: 1.458) and a 6 μm-thick core layer of $SiO_2.GeO_2$ (refractive index: 1.465) both of which were formed by CVD on a 1 mm-thick silicon substrate, the laminate being further bonded on the opposite side to a 1 mm-thick silicon substrate with a thermosetting resin, with subsequent curing. Three optical fibers were used, with the incident angle of an optical fiber 10a set to 69°, that of another optical fiber 10b to 65°, and that of the last optical fiber 10c to 73°, so that their optical axes intersected at one spot of an output face 9. The emitted light optical paths of the optical fibers 10 were 32 mm each. The incident angle measurement width per length of optical fiber was limited to 4° whereas the optical fiber had an emitted light expansion angle of 6°, because of the problem of measurement accuracy including blur of light at both extremities of expansion of emitted light. The refractive index measurement range of this sensor was 1.299 to 1.408. The length required for the output face was 2.3 mm.

Figure 5C:
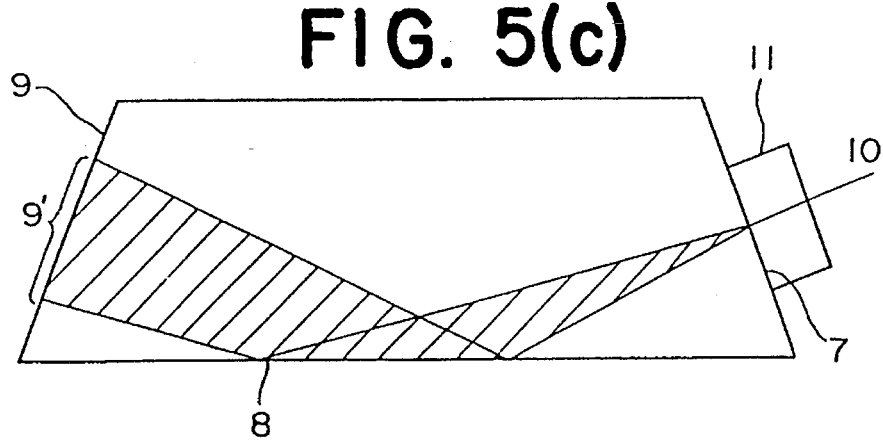

Also, a refractive index sensor of a single-reflection type which covers the same measurement range as the above embodiment, using a single optical fiber as shown in FIG. 5(c), was fabricated. The end of the optical fiber was polished so that the emitted light can have an expansion of 14°. The incident angle of the optical fiber 10 was 69°. The other conditions for fabrication were identical with those used above. The length required for the output face was 6.3 mm. This demonstrates that the use of three optical fibers shortens the length required for the output face.

Figure 6A:
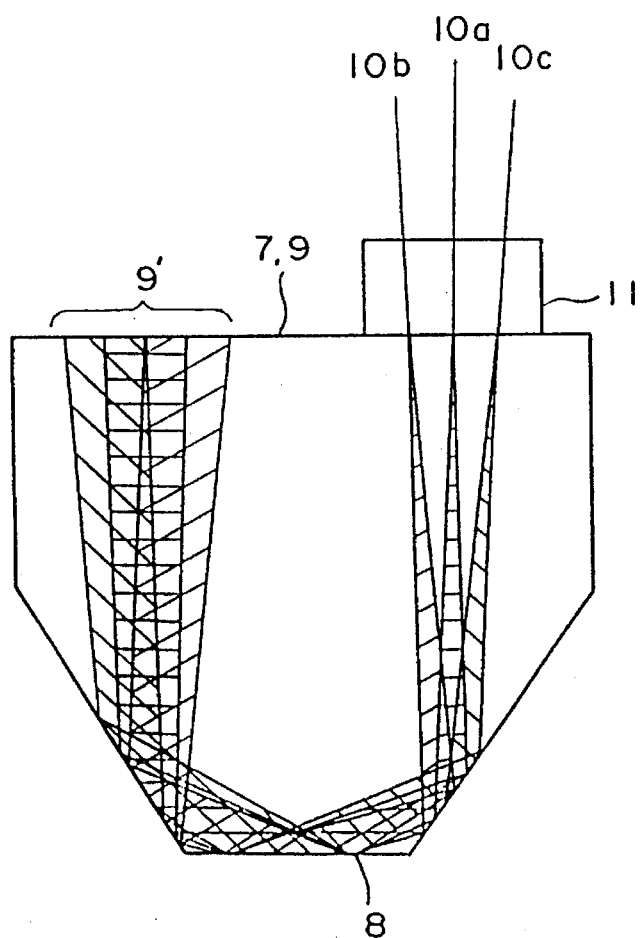
FIG. 6 gives schematic views of an embodiment of triple-reflection type sensor of the invention using a plurality of optical fibers, (a) when the points of intersection of optical axes of beams emergent from those optical fibers are arranged to be at one spot of the output face of the waveguiding layer, or (b) when the angle of expansion of an optical fiber is increased to such an extent that a single optical fiber obtains the same incident angle range as in the case (a) above.
Figure 6B:
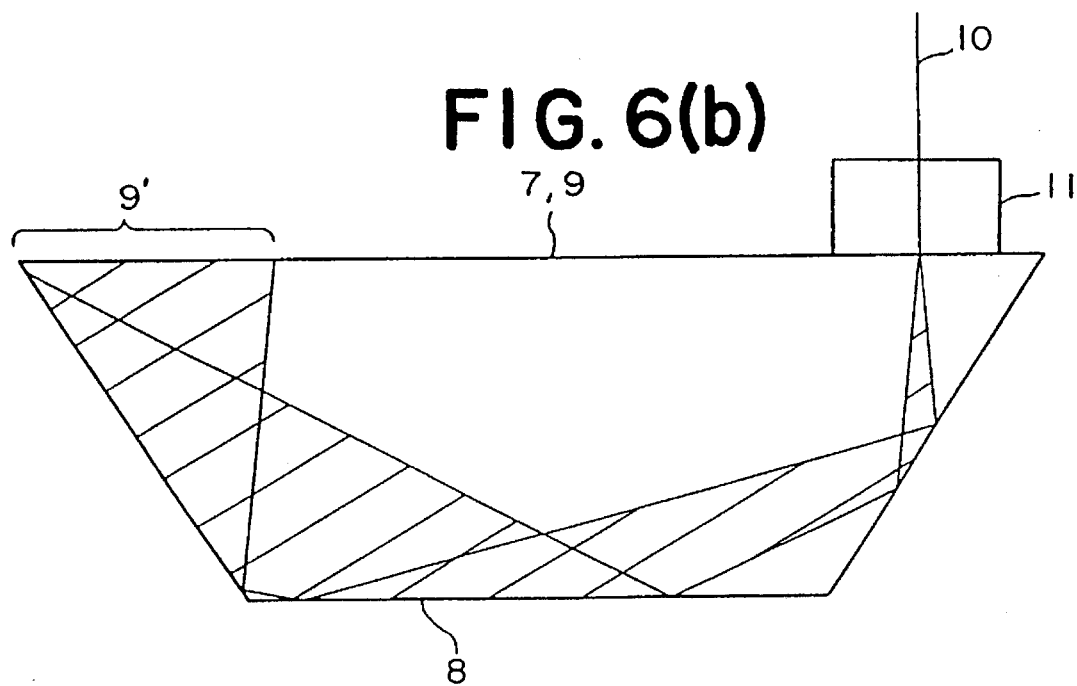

The total-reflection type refractive index sensor of the triple-reflection type structure shown in FIG. 3 can also be modified to use a plurality of optical fibers instead of one. Here, as FIG. 6(a) shows, it is desirable that the optical axes of the optical fibers 10a, 10b, and 10c intersect at one spot of the detection face 8. FIG. 6(b) depicts a typical total reflection pattern obtained with a single optical fiber having an expansion width of 12°. The light-output spot 9' is so broad that sometimes it overextends the output face. By setting the optical axes of optical fibers so that they intersect at one point on spot of the detection face as indicated in FIG. 6(a), it is possible to make the light-output spot properly smaller in area than in FIG. 6(b). Hence the measurement range can be broadened without the expense of a decrease in measurement accuracy.

A triple-reflection type sensor using three incidence optical fibers whose optical axes intersected at one spot of the detection face as in FIG. 6(a) was fabricated. The ends of the optical fibers were polished so that the emitted light has an expansion angle of 6° each. A waveguiding layer consisted of 20 μm-thick cladding layers of $SiO_2$ (refractive index: 1.458) and a 6 μm-thick core layer of $SiO_2.GeO_2$ (refractive index: 1.465) both of which were formed by CVD on a 1 mm-thick silicon substrate, the laminate being further bonded on the opposite side to a 1 mm-thick silicon substrate with a thermosetting resin, with subsequent curing. Three incidence optical fibers were used, with the incident angle of an optical fiber 10a set to 69°, that of another optical fiber 10b to 65, and that of the last optical fiber 10c to 73°, so that their optical axes intersected at one spot of a detection face. The emitted light optical paths of the optical fibers 1 were 32 mm each. The refractive index measurement range of this sensor was 1.299 to 1.408. The length required for the output face was 3.3 mm.

In contrast to the above, as shown in FIG. 6(b), a refractive index sensor of a triple-reflection type was made in the same way but using a single incidence optical fiber whose end was polished so that the emitted light could have an expansion of 14°, with the incident angle of the fiber set to 69°. The length necessary for the detection face was as long as 9.5 mm. This again proves that the use of three optical fibers reduces the length required for the output face.

Here too there is no hindrance to adjustments of the refractive index range by modification of the optical fiber end to a hemispherical lens or tip-rounded tapered shape by melt working or etching, provision of a waveguiding layer lens such as an optical fiber type lens/SELFOC lens adjacent to the input face, inside the waveguiding layer, or close to the output face, and/or by working of the detection face to a concave or convex contour.

According to the present invention, as described above, a total-reflection type refractive index sensor can be embodied as a single to triple-reflection type structure using from one optical fiber to a plurality of optical fibers. Under the invention, free choice of the refractive index measurement range to best suit the object of measurement is made possible through modifications of the refractive index of the waveguiding layer, angle of the input face, relative position of the input face and the detection face, and the number of optical fibers to be used.

As for the photodetector, normally a CCD photosensor or CCD photosensor array (one-dimensional CCD photosensor array) is disposed to read off the optical output. A translucent screen may be attached to the output face and monitor the laser beam projected on the screen visually or by means of a video camera. It is also possible to locate a chopper and a light receiver on the output face to read off the light output position.

Figure 9:
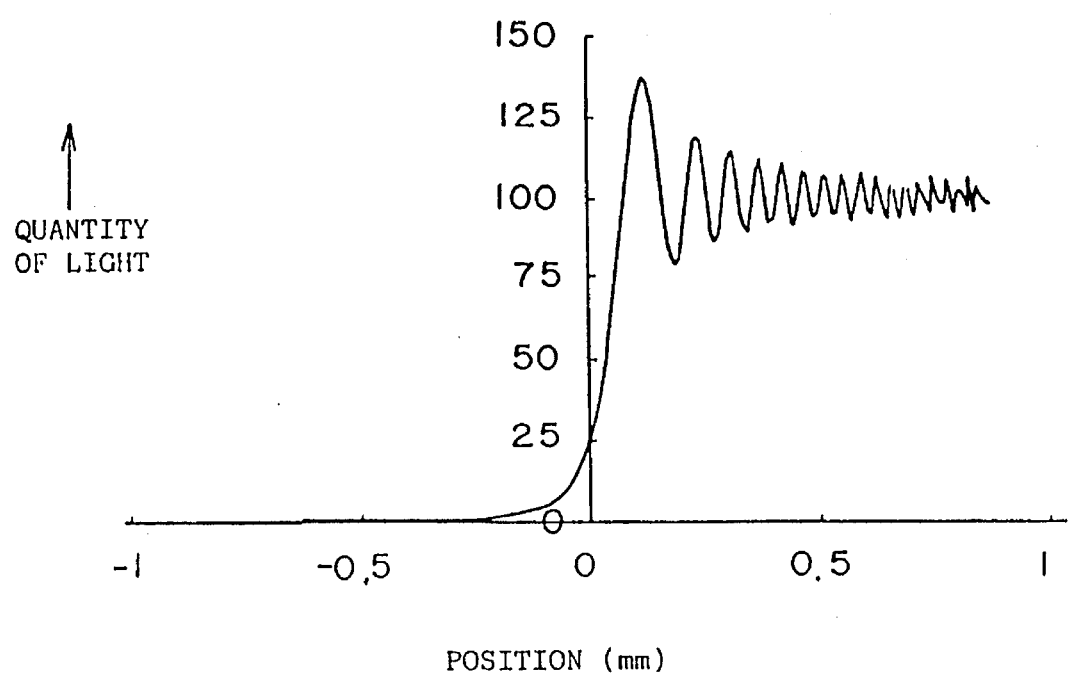
FIG. 9 is an intensity distribution curve of a Fresnel diffraction pattern on a half plane.

In reading out the light output position, it is necessary to exactly determine the bright-dark boundary correspondingly to the presence and absence of totally reflected light. By "bright-dark boundary" is meant the boundary between a region of total light reflection and a region where light is not totally reflected but is partly transmitted and reflected. This reading-out accuracy is an important factor contributing to the precision of the waveguide type refractive index sensor. For the determination of the bright-dark boundary, it is recommended to decide the bright-dark boundary from the point of intersection of reference light with measured waveform. Along the bright-dark boundary the Fresnel diffraction phenomenon occurs to shade it off. In determining the bright-dark boundary, it is convenient to exploit the Fresnel diffraction phenomenon in which the quantity of light of the measured waveform is always increased beyond that of the reference light. The point of intersection closest to the portion where the light quantity has increased between the reference waveform and the measured waveform is conveniently read out as the bright-dark boundary. In FIG. 7 is plotted the output waveform of a CCD photosensor array. The graph shows the details of the region of the bright-dark boundary position when the quantity of reflected light from an air face was measured as a reference waveform and n–$C_{13}H_{28}$ as a test material was placed in a cell and its reflected light quantity was measured. The 7–8 μs portion in the center is the region where the light quantity of the measured waveform was greater than that of the reference light owing to the Fresnel diffraction phenomenon. The position of the intersection point closest to the light-quantity increased portion is read out as the bright-dark boundary. For the determination of the intersection point position, there are three that can be adopted: (1) linear interpolation, (2) polynomial-curve interpolation, and (3) fitting. A CCD photosensor array has a multiplicity of CCD pixels arranged in length and width rows, each outputting the quantity of emitted light as a voltage value. By way of example the output values of pixels in the vicinity of a point of intersection of reference light with measured light are plotted in FIG. 8(a). In the case of linear interpolation, as depicted in FIG. 8(b), the point of split of a straight line connecting the pixel outputs on both sides of the intersection point of reference light and measured light curves is determined as the intersection point. In the polynomial-curve interpolation, as shown in FIG. 8(c), the intersection point is determined to be the point where a polynomial (quadratic or higher-degree) regression curve of a measured light curve at several points in the neighborhood of the intersection point intersects a reference light curve. In fitting, as in FIG. 8(d), a fitting curve of several to several ten points around the intersection point of reference light and measured light curves is found and then the bright-dark boundary is computed from the constants that constitute the equation of the fitting curve. The fitting curve is drawn by applying the theoretical expression of Fresnel diffraction in a half-plane to reflected light in the vicinity of the critical angle. FIG. 9 is an intensity distribution curve of a Fresnel diffraction pattern in a half-plane. The application of (2) polynominal-curve interpolation and (3) fitting improves the accuracy over (1) linear interpolation.

In reality, there arises a discrepancy between the bright-dark boundary and the intersection point of reference light and measured light, but it can be adjusted by computation. The expression for computation inside the measurement/computation unit 14 includes a term defining the refractive index of each pixel of the CCD, a term determining the intersection point of reference light and measured light curves, and an offset term for shifting the absolute value of refractive index. The discrepancy between the bright-dark boundary and the intersection point of reference light and measured light curves is corrected by the offset term.

Figure 10A:
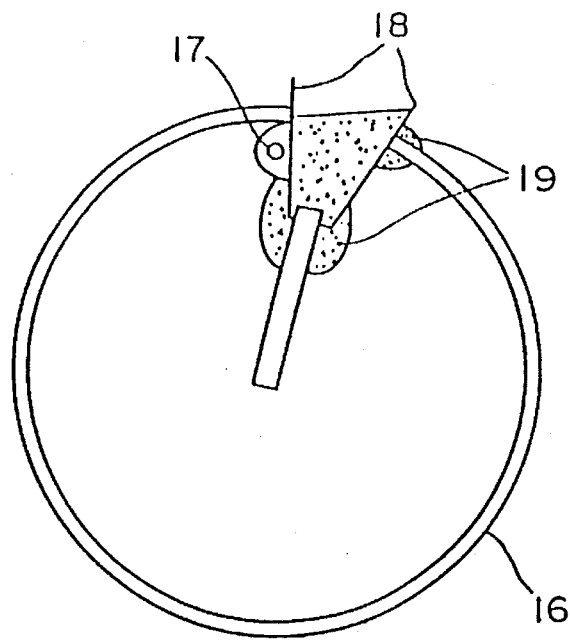
FIG. 10 illustrates a refractive index sensor of the invention in use; showing (a) the detail of mounting, (b) the sensor in the measuring position, and (c) in the washing position.
Figure 10B:
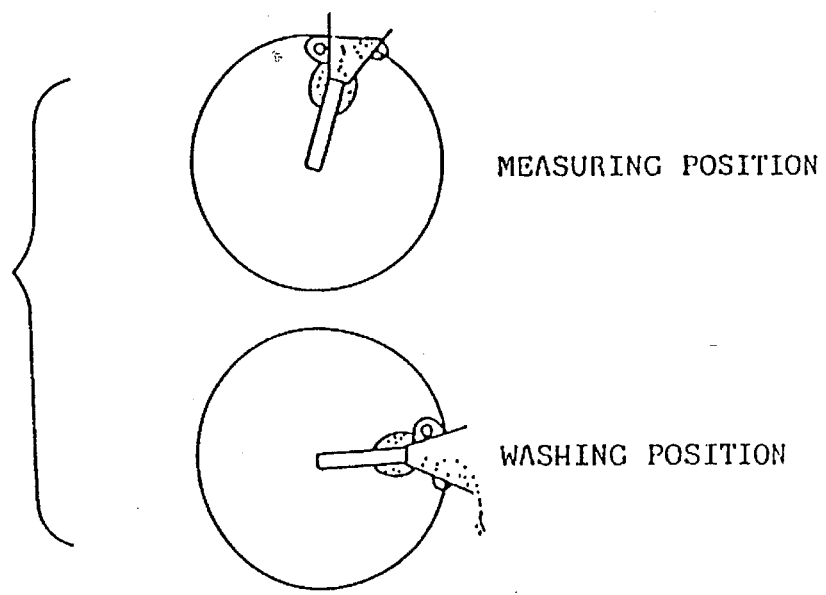

For use of a sensor of a single-reflection type structure shown in FIGS. 2 and 5, its sensor head assembly comprising a waveguiding layer substrate, optical fiber array, and CCD photosensor array is housed, e.g., as depicted in FIG. 10(a), in a cylindrical aluminum case 16 which is turnably located in place. A temperature sensor 17, e.g., a small Pt tip, is directly bonded to the substrate for the purpose of temperature measurement. In order to provide a receptacle for a test material, a recess is formed, e.g., by bonding silicon sheets 18 in a wide-V pattern to the sensor head assembly and the aluminum case. Fabrication of the receptacle from silicon sheets is beneficial for securing good heat transfer and preventing contamination due to the water and oil repellant properties of silicon. The sheets are properly bonded in position with adhesive 19. As illustrated in FIG. 10(b), measurement is made in the measuring position where the sensor shown above is directed substantially upwardly, and washing is done in the washing position where the sensor shown below is laid horizontally to be emptied and washed. Typical basic specifications of this sensor are:

Refractive index measurement range: 1.330–1.380

Refractive index display: 3.5 figures (1.nnn)

Refractive index measurement accuracy: ±0.003

Sample quantity required: 0.2–1.0 ml

Data display: real time

Figure 11A:
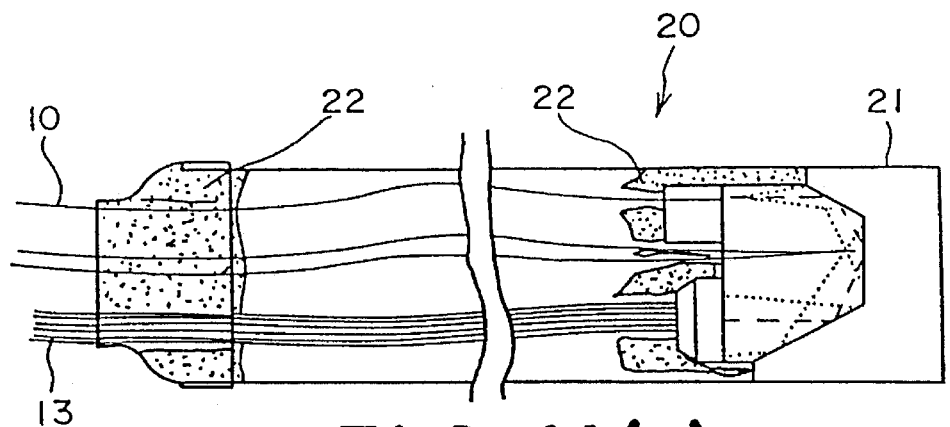
FIG. 11 illustrates a probe consisting of a sensor of the triple-reflection type shown in FIG. 3 embedded in a metal cylinder for continuous measurement during process; showing (a) the construction of the probe, (b) the front end of the head of the sensor, and (c) a measurement/computation control unit.
Figure 11B:
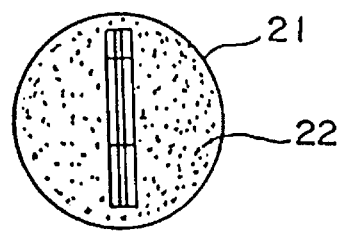
Figure 11C:
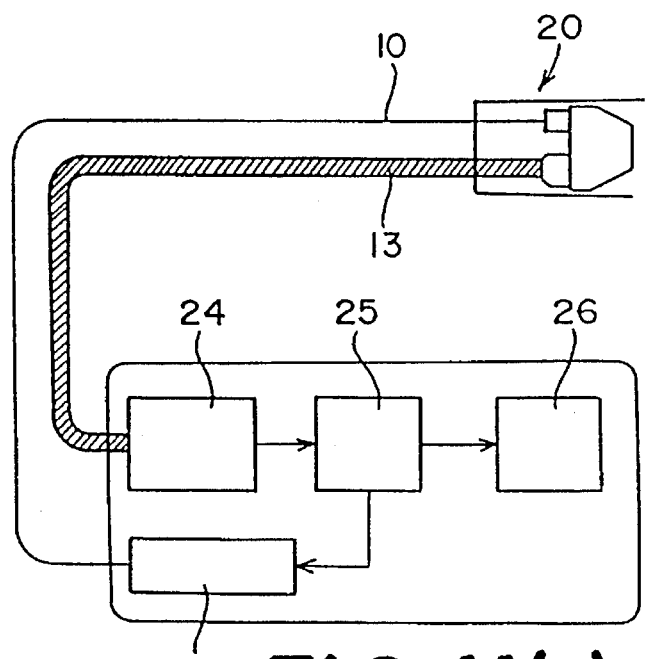
Figure 12:
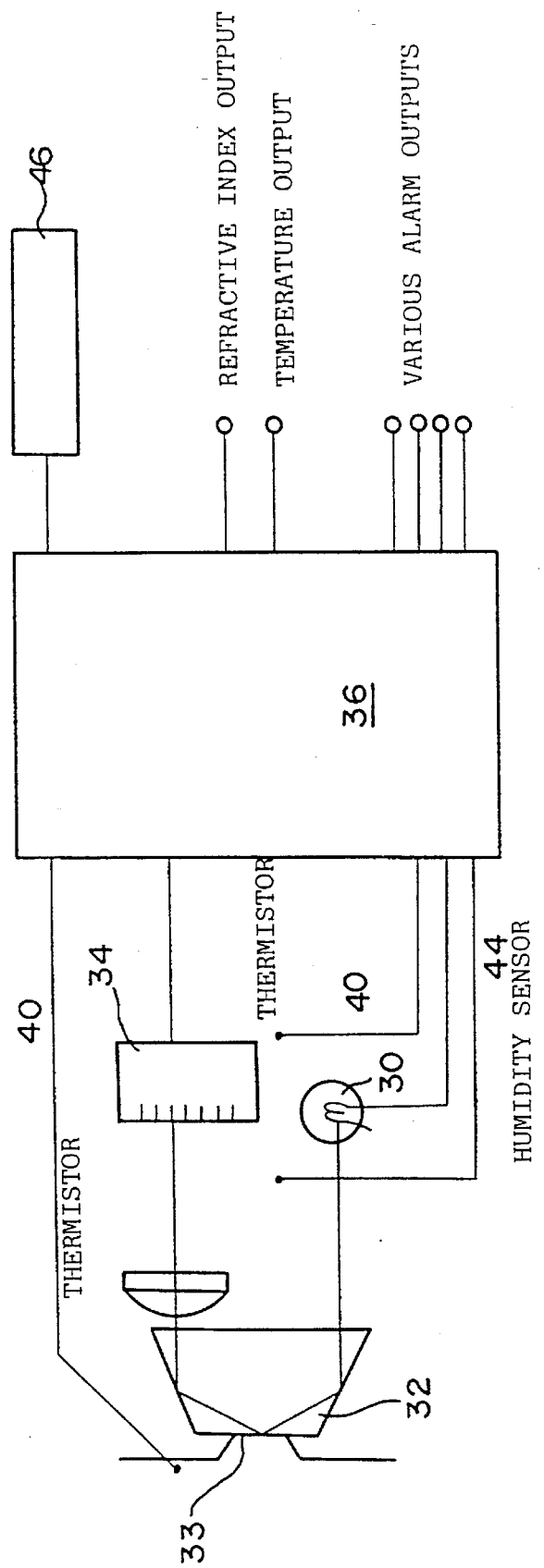
FIG. 12 is a block diagram of a detection unit according to Catalog Nos. 3621 and 3670 of a refractometer using a bulk prism which is marketed by ATAGO Co. as a process refractometer of PRM series.

FIG. 11(a) shows a probe 20 which consists of a refractive index sensor of a triple-reflection type of FIGS. 3 and 6 encased in a metallic outer cylinder 21 for continuous process measurement. A sensor head, optical fiber 10, and a digital signal cable 13 are secured to the metallic cylinder by a fixing material 22. To prevent light leakage during contact of the sensor with a test liquid, the exposed light-reflecting face is coated either with a thin metal film deposited by evaporation or with a coat of a material having a lower refractive index than the waveguide, e.g., an adhesive (thermosetting resin of a low refractive index) or a resin (silicon resin, etc.). FIG. 11(b) shows the front end of the sensor head. FIG. 11(c) shows a measurement control unit. The single-mode optical fiber, having an expansion angle of about 6°, is connected to a semiconductor laser source 23, e.g., a GaAs—AlGa—AS laser (wavelength: 0.85 μm). The digital signal cable 13 is connected through an interface circuit 24 to a microprocessor 25. This microprocessor 25 form at least a part of the measurement-computation unit. It gives a radiation command to the semiconductor laser source 23. Finally, the total reflection information is displayed by a display 26. Typical basic specifications of this sensor are:

Refractive index measurement range: 1.32–1.38

Refractive index display: 5.5 figures (1.nnnnn)

Refractive index measurement accuracy: ±0.00005

INDUSTRIAL APPLICABILITY

A continuous light incident angle to a detection face is achieved by ingeniously exploiting the expansion of light emitted from a single-mode optical fiber. A measurement range suited for a test material whose refractive index is to be measured can be set freely as desired by altering the refractive index of the waveguiding layer, angle of the input face, and relative position of the input face and the detection face. Since single-mode propagation of light through optical fiber is utilized, there is no allowance and hence measurement width high precision is accomplished. Thus, a small, high-precision refractive index sensor of a total-reflection type free of moving part is obtained. It is useful in off-line and on-line refractive index measurements on site in petroleum, chemical, petrochemical, food, and other manufacturing industries. Being of a total-reflection type, the sensor is capable of handling colored and low-transmissivity test materials as well.

The measurement range can be broadened without any sacrifice of measurement accuracy by connecting a plurality of optical fibers to the incidence side of the waveguiding layer, allotting separate measurement ranges to the individual fibers, and over-lapping those ranges. Also, if the intersection point of the optical axes of light beams from the individual optical fibers is set on one spot of the output face of the waveguiding layer, the length required for the output face can be made shorter than when a single optical fiber covers the same measurement range by increasing the angle of expansion of the light from the fiber. Similarly, with a sensor of a triple-reflection type, the length necessary for the detection face can be shorter than with a single optical fiber, only if the intersection point of the optical axes of light beams from the optical fibers is set on one spot of the detection face.

Specially, compared with the refractive index sensors using a bulk prism, as typified by the process refractive index sensors of PRM series marketed by ATAGO Co, the sensor of this invention offers the following advantages:

(1) The bulk prism necessitates a long measurement time because the heat capacity is so large that it takes much time to achieve thermal stabilization. According to the present invention, by contrast, the sensor itself is very small and uses a material of good thermal conductivity, such as silicon, for the substrate, and therefore faster thermal stabilization makes the measurement time shorter. This is particularly beneficial when the sensor is used for measurements batchwise, since changes in properties of the test material, e.g., by evaporation, can be avoided.

(2) Since the light intensity can be entrapped in the core by setting the thickness of the waveguiding layer so as to meet single-mode conditions, the reflected light becomes easier to detect. The bulk prism expands the light and makes the detection difficult.

(3) The present invention renders it easy to fabricate sensors with core layers of varied refractive indices, thereby to handle materials of different refractive indices.

(4) Laser beams can be employed as light sources. With a lamp source, its physical size inevitably produces a parallax even though a lens establishes parallelism. Consequently, the measurement accuracy decreases, with the detection end (boundary) out of focus. Under the invention, a laser beam is utilized, and a beam that has traveled through a single-mode optical fiber of about 6 μm core diameter is used as an optical source. The out-of-focus region at the detection end can be narrowed down, and, through more accurate determination of the bright-dark boundary, the measurement accuracy can be improved.

What is claimed is:

1. A refractive index sensor of a total-reflection type comprising a waveguiding layer of a cladding/core/cladding waveguide structure formed on a substrate, said waveguiding layer having
    (a) an input face connected to either
        (i) a single optical fiber, or
        (ii) a plurality of optical fibers which differ in angle of incidence but altogether form a continuous incident angle range,
        the single optical fiber or plurality of optical fibers injecting incident light having an expansion angle into the waveguiding layer,
    (b) a detection face which totally reflects/transmits the incident light from the optical fiber or fibers and which constitutes a surface with which a material whose refractive index is to be measured comes in contact, and
    (c) an output face which outputs the light reflected from the detection face, the output face being connected to optical detection means for detecting the refractive index of the material by determining a bright-dark boundary of the corresponding total reflected light from the detection face.

2. The sensor of claim 1 which is of a single-reflection type wherein the light from the input face is directly incident on the detection face, where the light is totally reflected/transmitted, and the reflected light from the detection face directly reaches the output face.

3. The sensor of claim 1 which is of a plural-reflection type wherein the light from the input face is totally reflected once or more times before incidence on the detection face, where the light is totally reflected/transmitted, and the reflected light from the detection face arrives at the output face either directly or after total reflection once or more times.

4. The sensor of claim 1 which is of a triple-reflection type wherein the input face and output face are combined flush with each other to be an input/output face parallel to the detection face, and the light from the incident position of the input/output face is totally reflected on one side to the detection face, where the light is totally reflected/transmitted, and the reflected light from the detection face is totally reflected on another side to reach the output position of the input/output face.

5. The sensor of claim 1 wherein the expansion angle of light is adjusted by working the end contour of the fiber.

6. The sensor of claim 1 wherein a waveguiding layer lens is provided between the optical fiber or plurality of optical fibers and the input face, or inside of the waveguiding layer.

7. The sensor of claim 1 wherein the detection face is worked to a concave or convex contour so as to adjust the refractive index range.

8. The sensor of claim 1 wherein the optical detection means is a CCD photosensor or CCD photosensor array.

9. The sensor of claim 8 wherein the optical detection means includes a measurement-computation unit which determines the bright-dark boundary using the linear interpolation, polynomial curve interpolation, or fitting method.

10. The sensor of claim 8 wherein the plurality of optical fibers are used and arranged so that the intersection point of the optical axes of the individual optical fibers intersect at one spot of the output face of the waveguiding layer or of the surface with which a material whose refractive index is to be measured comes in contact.

11. A refractive index sensor of a total-reflection type comprising a waveguiding layer of a cladding/core/cladding waveguide structure formed on a substrate, said waveguiding layer having
    (a) an input face connected to either
        (i) a single optical fiber of a single mode, or
        (ii) a plurality of optical fibers each of a single mode which differ in angle of incidence but altogether form a continuous incident angle range,
        the single optical fiber or plurality of optical fibers injecting incident light having an expansion angle into the waveguiding layer,
    (b) a detection face which totally reflects/transmits the incident light from the optical fiber or fibers and which constitutes a surface with which a material whose refractive index is to be measured comes in contact, and
    (c) an output face which outputs the light reflected from the detection face, the output face being connected to optical detection means for detecting the refractive index of the material by determining a bright-dark boundary of the corresponding total reflected light from the detection face.

12. The sensor of claim 11 which is of a single-reflection type wherein the light from the input face is directly incident on the detection face, where the light is totally reflected/transmitted, and the reflected light from the detection face directly reaches the output face.

13. The sensor of claim 11 which is of a plural-reflection type wherein the light from the input face is totally reflected once or more times before incidence on the detection face, where the light is totally reflected/transmitted, and the reflected light from the detection face arrives at the output face either directly or after total reflection once or more times.

14. The sensor of claim 11 which is of a triple-reflection type wherein the input face and output face are combined flush with each other to be an input/output face parallel to the detection face, and the light from the incident position of the input/output face is totally reflected on one side to the detection face, where the light is totally reflected/transmitted, and the reflected light from the detection face is totally reflected on another side to reach the output position of the input/output face.

15. The sensor of claim 11 wherein the expansion angle of light is adjusted by working the end contour of the fiber.

16. The sensor of claim 11 wherein a waveguiding layer lens is provided between the optical fiber or plurality of optical fibers and the input face, or inside of the waveguiding layer.

17. The sensor of claim 11 wherein the detection face is worked to a concave or convex contour so as to adjust the refractive index range.

18. The sensor of claim 11 wherein the optical detection means is a CCD photosensor or CCD photosensor array.

19. The sensor of claim 18 wherein the optical detection means includes a measurement-computation unit which determines the bright-dark boundary using the linear interpolation, polynomial curve interpolation, or fitting method.

20. The sensor of claim 18 wherein the plurality of optical fibers are used and arranged so that the intersection point of the optical axes of the individual optical fibers intersect at one spot of the output face of the waveguiding layer or of the surface with which a material whose refractive index is to be measured comes in contact.

* * * * *